Figure 1:
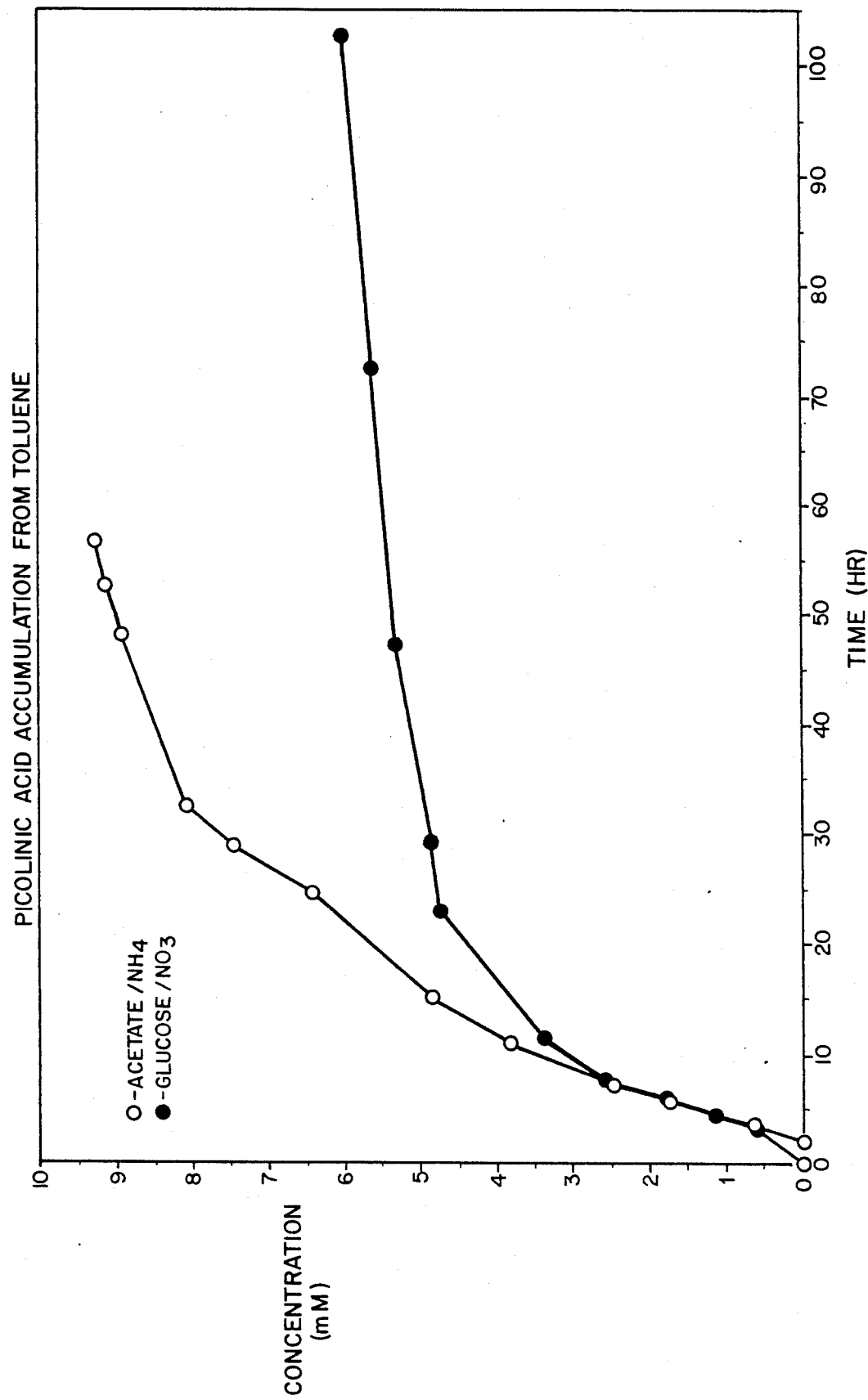

United States Patent [19]
Hagedorn et al.

[11] Patent Number: 4,859,592
[45] Date of Patent: Aug. 22, 1989

[54] PRODUCTION OF PICOLINIC ACID AND PYRIDINE PRODUCTS VIA PSEUDOMONAS

[76] Inventors: Scott R. Hagedorn, Old Coach Rd., Summit, N.J. 07087; Anthony J. East, 63 Niles Ave., Madison, N.J. 07940; Sol J. Barer, 271 White Oak Ridge Rd., Bridgewater, N.J. 08807

[21] Appl. No.: 759,038

[22] Filed: Jul. 26, 1985

[51] Int. Cl.$^4$ .................. C12P 17/12; C12N 1/20; C12R 1/40
[52] U.S. Cl. .................. 435/122; 435/253.3; 435/877
[58] Field of Search ............ 435/122, 253, 877, 253.3

[56] References Cited

U.S. PATENT DOCUMENTS 4,654,303  3/1987  Hagedorn ............ 435/172.3
4,666,841  5/1987  Hagedorn ............ 435/122
4,673,646  6/1987  Hagedorn ............ 435/146

OTHER PUBLICATIONS

Dagley, et al., "New Pathways in the Oxidative Metabolism of Aromatic Compounds by Micro-Organisms"; Nature, V. 188, pp. 560–566 (1960).
Moser et al., "Decarboxylation of 5-Substituted-2-Pyridinecarboxylic Acids", J. Org. Chem., V. 37, No. 24, pp. 3938–3940 (1972).

Primary Examiner—Elizabeth C. Weimar
Attorney, Agent, or Firm—Mathews, Woodbridge, Goebel, Pugh & Collins

[57] ABSTRACT

This invention provides a process for the bioconversion of a non-growth aromatic feed to an accumulated quantity of a picolinic acid product with reduced accumulation of 2-hydroxymuconic semialdehyde, and conducted in the presence of ammonium or a primary amine, which acid subsequently can be converted by chemical means to a pyridine product.

6 Claims, 2 Drawing Sheets

PRODUCTION OF PICOLINIC ACID AND PYRIDINE PRODUCTS VIA PSEUDOMONAS

BACKGROUND OF THE INVENTION

Heterocyclic compounds such as pyridine currently are recovered as constituents of coal tar, or are synthesized for example by the reaction of acetaldehyde with ammonia and formaldehyde to provide a pyridine, alpha-picoline and beta-picoline product mixture. Specialty heterocyclic aromatic chemicals are utilized in the production of adhesives, pesticides, vitamins, and the like. Another prospective route to heterocyclic aromatic compounds is by the reaction of ammonia or a primary amine with a 2-hydroxymuconic semialdehyde to form a picolinic acid:

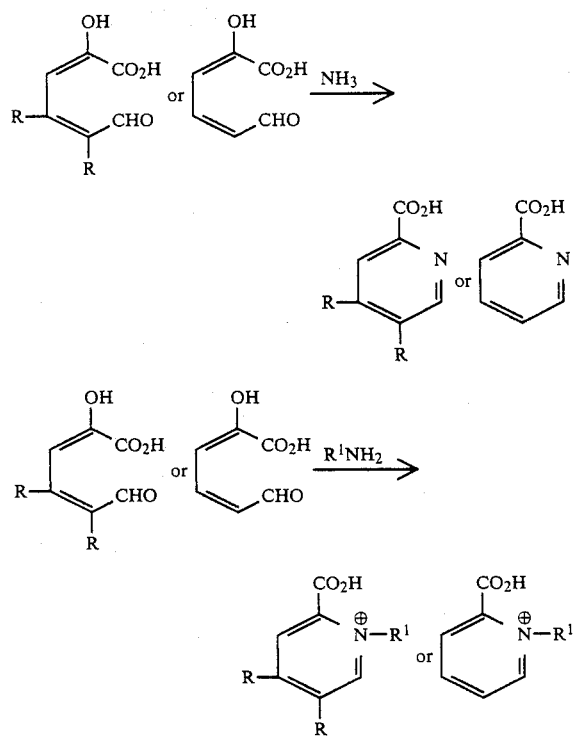

Subsequent decarboxylation of the picolinic acid could provide the corresponding pyridines and substituted pyridines, as illustrated in the Journal of Organic Chemistry, 37(24), 3938(1972) article by R. J. Moser et al.

A potentially convenient source of 2-hydroxymuconic semialdehyde is by the microbiological oxidation of various hydrocarbon substrates. Microbiological oxidation of aromatic substrates is reviewed by S. Dagley in Advances in Microbial Physiology, 6, 1–47(1971); by P. Chapman in "Degradation of Synthetic Organic Molecules In The Biosphere", pages 17–55, National Academy Of Sciences, 1972; and by P. Williams in "Microbial Degradation Of Xenobiotics And Recalcitrant Compounds" pages 97-107, Academic Press, 1981. Strains of microorganisms are known which metabolize aromatic hydrocarbon substrates by the meta pathway via catechol and 2-hydroxymuconic semialdehyde to biomass and carbon dioxide.

The Nature, 188, 560(1960) article by S. Dagley et al describes the cleavage of catechol by a solution of an enzyme, catechol 2,3-oxygenase, to produce a product with a yellow color in the bioconversion medium. The ultraviolet absorption spectrum indicates a 2-hydroxymuconic semialdehyde type product, which on standing with ammonium hydroxide forms alpha-picolinic acid.

The Canadian Journal Of Microbiology, 14, 1005(1968) article by R. S. Davis et al describes the metabolism of p-xylene and m-xylene by species of Pseudomonas. A metabolite is produced by a solution of enzyme which has an ultraviolet spectrum consistent with 2-hydroxymuconic semialdehyde structure. A solution of this metabolite treated with ammonium hydroxide yields a picolinic acid type product.

The Biochemical Journal, 106, 859(1968) publication by R. B. Cain et al also describes the formation of 5-methylpicolinic acid from 4-methylcatechol via 2-hydroxy-5-methylmuconic semialdehyde, utilizing a cell extract prepared from a microorganism grown on toluene sulfonate.

The Journal Of Bacteriology, 120(1), 31(1974) publication by G. J. Wigmore et al describes *Pseudomonas putida* mutants which metabolize phenol and cresols by the meta pathway via catechol and 2-hydroxymuconic semialdehyde intermediates. One mutant strain is described as being defective in both 2-hydroxymuconic semialdehyde hydrolase and dehydrogenase.

The potential of microbiological oxidation of an aromatic substrate such as toluene as a convenient source of 2-hydroxymuconic semialdehyde requires the construction of mutant strains of microorganisms which (1) metabolize an aromatic substrate via catechol or substituted catechol by means of the meta (catechol 2,3-oxygenase) pathway, and (2) allow the accumulation of a 2-hydroxymuconic semialdehyde type metabolite without its further assimilation to other metabolites. A solution of accumulated 2-hydroxymuconic semialdehyde metabolite is susceptible to chemical conversion to picolinic acid and pyridine products as illustrated above.

Accordingly, it is an object of this invention to provide a procedure for the bioconversion of an aromatic hydrocarbon by the meta pathway to 2-hydroxymuconic semialdehyde or substituted 2-hydroxymuconic semialdehyde, and for the in situ formation of a picolinic acid product.

It is another object of this invention to provide a microbial culture which is capable of metabolizing toluene, substituted toluene, catechol, or substituted catechol to 2-hydroxymuconic semialdehyde or substituted 2-hydroxymuconic semialdehyde metabolite quantitatively.

It is another object of this invention to provide a process for the synthesis of a picolinic acid product from an aromatic hydrocarbon via a biosynthesized 2-hydroxymuconic semialdehyde intermediate.

It is a further object of this invention to provide a process for the synthesis of a pyridine product from an aromatic hydrocarbon via 2-hydroxymuconic semialdehyde and picolinic acid intermediates.

The present invention subject matter is related to that described in U.S. Pat. No. 4,666,841.

Other objects and advantages of the present invention shall become apparent from the accompanying description and examples.

DESCRIPTION OF THE INVENTION

One or more objects of the present invention are accomplished by the provision of a process for the production of a picolinic acid product which comprises supplying (1) toluene or substituted toluene, (2) molecular oxygen, and (3) ammonia or a primary amine to a bioconversion medium containing a microbial culture which possesses active catechol 2,3-oxygenase and which exhibits no enzymatic activity that metabolizes 2-hydroxymuconic semialdehyde or substituted 2-hydroxymuconic semialdehyde, to produce and accumulate a picolinic acid product.

As further described herein, an alternative preferred type of non-growth carbon source is catechol or substituted catechol. The catechol chemical structure corresponds to one of the intermediate metabolites formed when toluene or substituted toluene is bioconverted by a present invention microorganism to 2-hydroxymuconic semialdehyde via the meta metabolic pathway. Toluene is oxidized to 2-hydroxymuconic semialdehyde via a series of benzyl alcohol, benzaldehyde, benzoic acid, hydrodihydroxybenzoic acid and catechol intermediates. The active enzymes include toluene monooxygenase, benzyl alcohol dehydrogenase, benzaldehyde dehydrogenase, benzoic acid dioxygenase, hydrodihydroxybenzoic acid dehydrogenase and catechol 2,3-oxygenase.

In another embodiment, this invention provides a process for the production of a picolinic acid product which comprises supplying (1) catechol or substituted catechol, (2) molecular oxygen, and (3) ammonia or a primary amine to a bioconversion medium containing a microbial culture which possesses active catechol 2,3-oxygenase and which exhibits no enzymatic activity that metabolizes 2-hydroxymuconic semialdehyde or substituted 2-hydroxymuconic semialdehyde, to produce and accumulate a picolinic acid product.

In another embodiment, this invention provides a process for the production of a picolinic acid product which comprises supplying (1) an aromatic hydrocarbon corresponding to the formula:

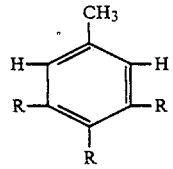

where R is hydrogen or an alkyl group containing between about 1-4 carbon atoms, (2) molecular oxygen, and (3) ammonia or a $R^1$—$NH_2$ primary amine to a bioconversion medium containing a microbial culture of a strain which has been constructed to possess catechol 2,3-oxygenase with activity that is not inhibited in the presence of less than about 0.1 gram of 2-hydroxymuconic semialdehyde per liter of bioconversion medium, and which lacks active catechol 1,2-oxygenase, 2-hydroxymuconic semialdehyde hydrolase and 2-hydroxymuconic semialdehyde dehydrogenase, to produce and accumulate a picolinic acid product corresponding to the formula:

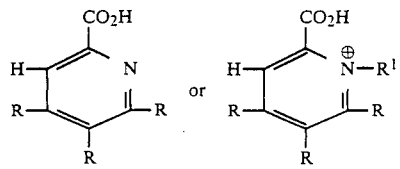

where R is as previously defined, and R1 is a substituent selected from aliphatic, alicyclic and aromatic groups.

In another embodiment, this invention provides a process for the production of a picolinic acid product which comprises supplying (1) a dihydric phenol corresponding to the formula:

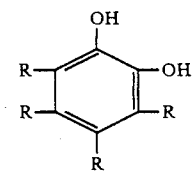

where R is hydrogen or an alkyl group containing between about 1-4 carbon atoms, (2) molecular oxygen, and (3) ammonia or a $R^1$—$NH_2$ primary amine to a bioconversion medium containing a microbial culture of a strain which has been constructed to possess catechol 2,3-oxygenase with activity that is not inhibited in the presence of less than about 0.1 gram of 2-hydroxymuconic semialdehyde per liter of bioconversion medium, and which lacks active catechol 1,2-oxygenase, 2-hydroxymuconic semialdehyde hydrolase and 2-hydroxymuconic semialdehyde dehydrogenase, to produce and accumulate a picolinic acid product corresponding to the formula:

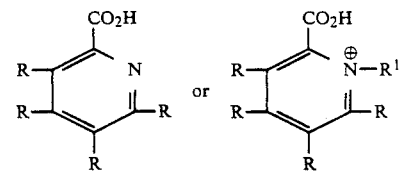

where R is as previously defined, and $R^1$ is a substituent selected from aliphatic, alicyclic and aromatic groups.

In another embodiment, this invention provides a process for the production of a pyridine product which comprises supplying (1) toluene or substituted toluene, (2) molecular oxygen, and (3) ammonia or primary amine to a bioconversion medium containing a microbial culture which possesses active catechol 2,3-oxygenase and which exhibits no enzymatic activity that metabolizes 2-hydroxymuconic semialdehyde or substituted 2-hydroxymuconic semialdehyde, to produce and accumulate a picolinic acid product; and subjecting the picolinic acid product to heating at a temperature sufficiently elevated to decarboxylate the picolinic acid product to the corresponding pyridine product.

In another embodiment, this invention provides a process for the production of a pyridine product which comprises supplying (1) an aromatic hydrocarbon corresponding to the formula:

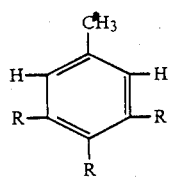

where R is hydrogen or an alkyl group containing between about 1-4 carbon atoms, (2) molecular oxygen, and (3) ammonia or a $R^1$—$NH_2$ primary amine to a bioconversion medium containing a microbial culture which has been modified to possess catechol 2,3-oxygenase with activity that is not inhibited in the presence of less than about 0.1 gram of 2-hydroxymuconic semialdehyde per liter of bioconversion medium, and which lacks active catechol 1,2-oxygenase, 2-hydroxymuconic semialdehyde hydrolase and 2-hydroxymuconic semialdehyde dehydrogenase, to produce and accumulate a picolinic acid product corresponding to the formula:

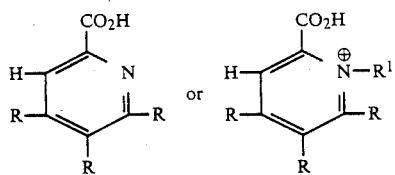

where R is as previously defined, and $R^1$ is a substituent selected from aliphatic, alicyclic and aromatic groups; and heating the picolinic acid product at a temperature between about 60°-200° C. to decarboxylate the picolinic acid to a pyridine product corresponding to the formula:

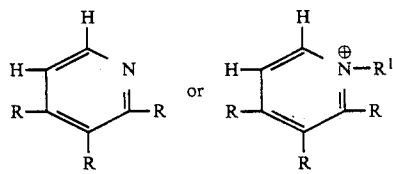

In a further embodiment, this invention provides a process for the production of a pyridine product which comprises supplying (1) catechol or substituted catechol, (2) molecular oxygen, and (3) ammonia or primary amine to a bioconversion medium containing microbial culture which possesses active catechol 2,3-oxygenase and which exhibits no enzymatic activity that metabolizes 2-hydroxymuconic semialdehyde or substituted 2-hydroxymuconic semialdehyde, to produce and accumulate a picolinic acid product; and subjecting the picolinic acid product to heating at a temperature sufficiently elevated to decarboxylate the picolinic acid product to the corresponding pyridine product.

Microorganism Construction Procedures

A detailed elaboration of methods of microbe construction is disclosed in U.S. Pat. No. 4,654,303 incorporated herein by reference.

In the construction process, the starting microorganism can be any organism capable of growth on the selected aromatic substrate and possessing active catechol 2,3-oxygenase, e.g., a Pseudomonad. A variety of gram negative organisms have these traits including some members of the species Pseudomonas putida, Pseudomonas aeruginosa and Pseudomonas fluorescens; and some members of the genera Azotobacter, Klebsiella and Serratia.

The metabolism of toluene, m-xylene and p-xylene is performed by the enzymes of genes (Xyl A - Xyl G) normally encoded on a TOL plasmid. Toluene and p-xylene can be metabolized by either the Xyl F or Xyl G gene encoded enzymes. m-Xylene is committed to metabolism by the Xyl F gene encoded enzyme due to the inherent chemical structure of the metabolic intermediates. Toluene (but not p-xylene or m-xylene) can be metabolized by chromosomal ortho pathway enzymes, as reported by D. A. Kunz et al, Journal of Bacteriology, 146, 952(1981).

The mutant construction strategy is first to block the metabolism of benzoate on the chromosome. A wild type TOL plasmid then is introduced into the mutant microorganism. Selection is made for a mutant defective in Xyl F and unable to grow on m-xylene, but which still grows on toluene and p-xylene via the Xyl G encoded enzyme. A mutant of the Xyl F defective strain is isolated, which is mutant in Xyl G, and which allows the accumulation of 2-hydroxymuconic semialdehyde from the metabolism of an aromatic substrate such as toluene.

The growth medium consists of 91.2 mM $Na_2HPO_4$, 58.8 mM $KH_2PO_4$, 15.1 mM $(NH_4)_2SO_4$, 2.46 g/l $MgSO_4.7 H_2O$, 1.1 g/l $CaCl_{22}.6H_2O$ and 0.0268 g/l $FeSO_4$, with a pH of 7.0 (NO medium). The appropriate water soluble carbon sources are added in the range of 5–10 mM.

Growth of microorganisms on aromatic hydrocarbons in liquid cultures is achieved by adding the hydrocarbon to pre-sterilized polypropylene nitrogen storage vials and placing the vials in shake flasks. Growth of microorganisms on aromatic hydrocarbonsor solid media is accomplished by adding 2% agar to the above described NO medium prior to sterilization. Hydrocarbon is provided by placing a glass vial containing the appropriate hydrocarbon in the lid of a Petri dish containing the agar minimal media.

Growth typically is measured by determining the turbidity of the cell suspension in a Klett-Summerson Chlorimeter using the #66 red filter. One Klett unit is equivalent to about 3.5 mg dry weight per liter. Cultures are stored with 10 percent glycerol under liquid nitrogen.

Induction of mutants unable to grow on the hydrocarbons is accomplished by growing the culture in Luria broth overnight with a vial of the liquid hydrocarbon.

For whole cell oxygen uptake assay, 50 ml of a cell suspension of an optical density of 200–300 klett units is centrifuged, washed and resuspended in 5.0 ml, 50 mM phosphate buffer (pH 7.9) and 0.1% antifoam. The concentrated cell suspension is oxygenated with pure oxygen for two minutes. 2.0 ml of the oxygenated cell suspension is used in a Clark oxygen electrode (Yellow Springs Instrument Co.), and the endogenous rate of oxygen uptake is recorded. 30 μl of 10 mM substrate is then added and the increased rate oxygen uptake is measured.

For preparation of cell extracts, 1.0 g of a frozen cell suspension is thawed in 2.0 ml of 50 mM phosphate buffer, pH 7.0. The thawed cell suspension is passed through a French pressure cell followed by treatment with DNase (1.0 mg) and RNase (1.0 mg) for 10 minutes at room temperature. The extract is then centrifuged at 12,000 ×g for 15 min. at 5° C., and the supernatant is used for enzyme assays.

For enzyme assays 2-hydroxymuconic semialdehyde (HMSA) is prepared using 60 nmoles of catechol in 1.0 ml of 50 mM phosphate buffer, pH 7.0, and 10–50 μl of a cell extract of toluene induced mutant (defective in Xyl G and Xyl F). The catechol is oxidized to completion as determined by no further increase in absorbance at 375 nm, and used to assay for HMSA hydrolase and HMSA dehydrogenase.

The construction procedure is adapted to provide a microbial culture which possesses active catechol 2,3-oxygenase with activity that is not inhibited in the presence of a low level of 2-hydroxymuconic semialdehyde per liter of bioconversion medium, and which lacks active muconate lactonizing enzyme, 2-hydroxymuconic semialdehyde hydrolase and 2-hydroxymuconic semialdehyde dehydrogenase.

A herein described microbial culture is capable of metabolizing an aromatic substrate selected from toluene and substituted toluene by the meta pathway via catechol or substituted catechol to 2-hydroxymuconic semialdehyde or substituted 2-hydroxymuconic semialdehyde, and it possesses catechol 2,3-oxygenase activity that is not inhibited in the presence of a low level of 2-hydroxymuconic semialdehyde or substituted 2-hydroxymuconic semialdehyde in a bioconversion medium, and it exhibits no enzymatic activity that metabolizes 2-hydroxymuconic semialdehyde or substituted 2-hydroxymuconic semialdehyde. This type of microbial culture is also capable of bio-oxidizing catechol or substituted catechol quantitatively to accumulate 2-hydroxymuconic semialdehyde or substituted 2-hydroxymuconic semialdehyde.

Illustrative of suitable microorganisms are constructed strains of microorganisms, e.g., fluorescent Pseudomonads, each of which has the following characteristics:

(a) possesses active catechol 2,3-oxygenase;
(b) lacks active muconate lactonizing enzyme;
(c) lacks active 2-hydroxymuconic semialdehyde hydrolase;
(d) lacks active 2-hydroxymuconic semialdehyde dehydrogenase; and
(e) cells are rod shaped, vigorously motile and polarly flagellated.

Novel strains of *Pseudomonas putida* Biotype A having the above recited characteristics have been deposited with the American Type Culture Collection (12301 Parklawn Drive, Rockville, Md. 20852) in compliance with MPEP 608.01(p)C and have been accorded accession numbers ATCC 39213 and ATCC 39636.

A constructed mutant strain (e.g., *Pseudomonas putida* Biotype A, strain ATCC 39636) has characteristics which are unique for the microbiological conversion of toluene or substituted toluene for the production and accumulation of 2-hydroxymuconic semialdehyde or substituted analog of 2-hydroxymuconic semialdehyde at a high rate and concentration.

First, the parent microorganism is capable of growing at a rapid rate, e.g., a growth doubling time of about two hours on toluene or substituted toluene.

Second, the mutant microorganism metabolizes toluene or substituted toluene by the meta pathway via catechol cleavage by the action of catechol 2,3-oxygenase. Concomitantly only induced catechol 1,2-oxygenase appears in the microorganism culture.

Third, the catechol 2,3-oxygenase activity is not repressed or inhibited by the presence of a low level of a 2-hydroxymuconic semialdehyde metabolite, e.g., a level of metabolite less than about 0.1 gram/liter in the bioconversion medium. This permits the accumulation of 2-hydroxymuconic semialdehyde at a level which is higher than about 0.1 gram/liter of medium.

Fourth, the meta pathway series of conversion reactions is blocked subsequent to the formation of the 2-hydroxymuconic semialdehyde from catechol. The mutant microorganism lacks the presence of active muconate lactonizing enzyme, 2-hydroxymuconic semialdehyde hydrolase and 2-hydroxymuconic semialdehyde dehydrogenase enzymes. Hence, the 2-hydroxymuconic semialdehyde metabolite is able to accumulate as it is produced, until the level of metabolite in the bioconversion medium inhibits the activity of the enzymes in the toluene oxidation pathway, i.e., the 2-hydroxymuconic semialdehyde metabolite accumulates up to a level of about one gram per liter of bioconversion medium. No microorganism is reported in the literature as able to produce and accumulate a 2-hydroxymuconic semialdehyde metabolite to these levels from an aromatic hydrocarbon substrate or any other aromatic substrate.

Microbial cultures described herein have an inherent genetic characteristic in common, i.e., each microbial culture is capable of biologically oxidizing toluene or catechol, or substituted toluene or catechol, quantitatively by the meta pathway to an accumulated quantity of 2-hydroxymuconic semialdehyde or substituted 2-hydroxymuconic semialdehyde in a bioconversion system. The quantity of 2-hydroxymuconic semialdehyde metabolite accumulated is at least between about 0.1–1 gram per liter of bioconversion medium.

2-Hydroxymuconic Semialdehyde Production And In Situ Formation Of Picolinic Acid Aromatic substrates that can be bioconverted to 2-hydroxymuconic semialdehyde and related metabolites include toluene, m-xylene, p-xylene, 4-ethyltoluene, 4-fluorotoluene, 4-methoxytoluene, mesitylene, benzyl alcohol, benzaldehyde, benzoic acid, catechol, 4-methylcatechol, and the like.

The rate of aromatic substrate (e.g., toluene or catechol) conversion with a constructed mutant microbial culture typically is at least about 100–200 milligrams of 2-hydroxymuconic semialdehyde produced per dry weight gram of cells per hour. The conversion of non-growth aromatic feedstock proceeds readily at a dry weight cell concentration between about 1–50 grams per liter, with a resultant 2-hydroxymuconic semialdehyde production rate of at least about 100–200 milligrams per liter per hour. As demonstrated in the Examples and Figures, the formed 2-hydroxymuconic semialdehyde converts in situ to the corresponding picolinic acid product.

The ammonium ions or primary amine component in the bioconversion medium is supplied in an excess of the nutrient requirements of the culture, i.e., the nitrogen required for cell growth and energy. In a typical bioconversion medium of the present invention, an excess of ammonium or primary amine will be in the range between about 10–100 millimolar. The ammonium or primary amine is present in an amount which is at least sufficient to react with the 2-hydroxymuconic semialdehyde that forms, and yield the desired picolinic acid product in situ.

Suitable primary amines which may be utilized include $C_1$-$C_{12}$ compounds such as methylamine, ethylamine, hexylamine, decylamine, allylamine, cyclohexylamine, aniline, anisidine, naphthylamine, and the like.

It is advantageous to conduct the bioconversion process under nutrient limited conditions to achieve a higher accumulated yield of picolinic acid via the formed 2-hydroxymuconic semialdehyde, whereby the microbial population is stabilized by the prevention of a growth advantage for revertants which are capable of growing on the aromatic substrate (e.g., toluene). These conditions can be accomplished by limiting the supply of sulfur to the bioconversion medium.

The bioconversion system generally is buffered to provide an approximately neutral pH in the aqueous medium, e.g., a pH in the range of about 6-8.

Under optimal conditions, the 2-hydroxymuconic semialdehyde formation and conversion to picolinic acid can approach up to about one gram of picolinic acid per liter of bioconversion medium. The microbiological oxidation process normally is conducted at ambient temperatures up to about 31° C.

The picolinic acid metabolite can be recovered from the bioconversion medium by conventional means, such as by extraction of the acidified aqueous medium with an organic solvent after the cells have been removed. Alternatively, the picolinic acid can be recovered as a cell-free aqueous solution, in which medium the picolinic acid can be subjected to chemical treatment to form other products.

Production Of Pyridine Products

In a typical procedure, the bioconversion medium is either centrifuged or passed through an ultrafiltration unit to separate the microbial cells from the aqueous liquid phase. The aqueous medium contains accumulated picolinic acid metabolite.

The subsequent conversion of picolinic acid or substituted picolinic acid to the corresponding pyridine product is accomplished by heating the aqueous solution of the picolinic acid under conditions which achieve decarboxylation of the picolinic acid. Suitable decarboxylation conditions are described in the Canadian Journal of Chemistry, 50, 3017(1972) publication by G. E. Dunn et al.

In a typical procedure, the aqueous solution of picolinic acid is acidified to a pH of less than about 3 with a reagent such as phosphoric acid, and the aqueous solution is autoclaved at 100° -150° C. until the decarboxylation reaction is completed, e.g., a reaction period of about 0.5-5 hours.

For product recovery, the aqueous product medium can be neutralized and the pyridine product recovered by distillation. When the product is N-substituted, i.e., it is a quaternary ammonium salt compound, then the product can be recovered as a residue after evaporation of the aqueous medium, followed by crystallization from a solvent medium or other suitable purification techniques.

As an alternative procedure, the picolinic acid can be recovered from the bioconversion medium, and subjected to pyrolysis conditions to effect the desired decarboxylation reaction.

The following examples are further illustrative of the present invention. The components and specific ingredients are presented as being typical, and various modifications can be derived in view of the foregoing disclosure within the scope of the invention.

As a general procedure, a series 500 LH Engineering chemostat with a 1.7 liter vessel is used in the fermentation studies. The media is 75 mM phosphate plus mineral salts with either 4.25 mM $(NH_4)_2SO_4$ or 8.50 mM $NaNO_3$ as the nitrogen source. The fermentor is inoculated with 10 ml of an overnight Luria broth culture of the desired organism with the appropriate carbon source and grown overnight batchwise. Continuous addition of the media is initiated at a dilution rate of 0.20 $hr^{-1}$, and the culture is allowed to grow continuously overnight. The next day, the addition of liquid aromatic substrate is started by sparging the liquid substrate with air at a rate of 0.3 $ft^3$ per hour.

2-Hydroxymuconic semialdehyde is analyzed by UV spectrophotometry by diluting 10-100 μl into 1.0 ml 50 mM phosphate (pH 7.0) and scanning the spectrum from 400 nm-340 nm. The absorbance is measured at the absorbance maximum, 375 nm, and the concentration calculated using the extinction coefficient of $\epsilon = 36.5$ $mM^{-1}$ $cm^{-1}$.

Picolinic acid is determined by high pressure liquid chromatography (HPLC) using a C18 reverse phase column in a Waters radial compression module. Phosphoric acid (0.1%) with 5% isopropanol is used as the solvent at a flow rate of 1 ml/min. This gives picolinic acid a retention time of 4-5 minutes.

EXAMPLE I

This Example illustrates the isolation of toluene oxidizing microorganisms as described in U.S. 4,355,107.

Soil samples are collected from a variety of areas and added to medium plus paraffin containing toluene. After shaking at 28° C. for 24 hours growth is apparent in the medium. Strains are isolated by streaking on agar plates containing a vial of toluene in the lid. Colonies appeared on the agar after approximately 36 hours. The size of these colonies range from 1 to 5 mm. A representative sampling of these colonies is taken and cultures are stored under liquid nitrogen for long-term preservation.

A strain derived from one of the largest colonies is chosen for further work and designated MW 1000. This strain is identified as a *Pseudomonas putida* Biotype A on the basis of the following criteria:

(a) the cells are rod shaped, vigorously motile and polarly flagellated;
(b) cells grows well on benzoate and p-hydroxybenzoate;
(c) cell growth on benzoate induces the synthesis of carboxymuconate lactonizing enzyme and carboxymuconolactone decarboxylase but not protocatechuate oxygenase, a pattern of regulation characteristic only of the *Pseudomonas putida* Biotype A;
(d) the induced enzyme muconolactone isomerase, carboxy-muconate lactonizing enzyme, and carboxymuconolactone decarboxylase are immunologically identical with those enzymes synthesized by *Pseudomonas putida* Biotype A, a saprophytic organism extensively studied in the literature.

A growth study of MW 1000 on toluene is conducted and it is found that the organism grows with a doubling time of approximately 3.5 hours and has a 5 hour lag period. Toluene grown MW 1000 consumes oxygen when presented with toluene, benzyl alcohol, benzaldehyde, m-toluate or catechol. With catechol the medium turns yellow indicating the production of excess 2-hydroxymuconic semialdehyde.

The presence of the meta pathway is confirmed by demonstration of catechol 2,3-oxygenase activity in cell free extracts and a failure to demonstrate the catechol 1,2-oxygenase even after inactivation of the 2,3-oxygense by treatment with hydrogen peroxide. MW 1000 also oxidizes benzoate via the meta pathway following induction with benzoate.

MW 1200 is a mutant of MW 1000 which is constitutive for toluate oxidation. It is obtained by growing MW 1000 in enrichment cycles on m-toluate. MW 1200 exhibits a higher catechol 2,3-oxygenase activity than MW 1000.

EXAMPLE II

This Example illustrates the construction of a *Pseudomonas putida* Biotype A strain ATCC 39213 and strain ATCC 39636 type mutants which are capable of oxidizing toluene to accumulated 2-hydroxymuconic semialdehyde (HMSA) via the meta (catechol 2,3-oxygenase) pathway.

The starting microorganism is the *Pseudomonas putida* Biotype A mutant strain MW 1200 described in Example I.

Strain MW 1200 is subjected to 60 generations of growth on benzoate which selects for loss of the TOL plasmid. The "cured" strain isolated by this procedure metabolizes benzoate via the chromosomal ortho pathway rather than the plasmid meta pathway, and no longer grows on toluene, p-xylene, m-xylene, p-toluate or m-toluate. This strain is designated BAC and its streptomycin derivative is designated BACS.

BACS is mutagenized with N-methyl-N'-nitrosoguanidine (NNG), selected against growth on benzoate with amoxicillin and D-cycloserine, and plated onto 5 mM benzoate plus 0.5 mM succinate. Small colonies on this media are tested for growth on benzoate and catechol. A mutant unable to grow on benzoate is shown by enzyme assay to be defective in muconate lactonizing enzyme (cat B) and designated BACS 2-4.

A TOL plasmid (pWWO) is transferred by conjugation from PaW15 (a leucine auxotroph) to BACS 2-4. A single colony of PaW15 is used to inoculate liquid NO medium containing 1 mM leucine plus a vial of toluene, and is grown overnight. A single colony of BACS 2-4 from a nutrient agar plate is inoculated into Luria Broth and grown overnight. 5 ml of each overnight culture are mixed and filtered onto a presterilized Millipore filter (0.45 μm), placed on a nutrient agar plate and incubated overnight at 30° C. Controls consist of 5 ml samples of PaW15 and BACS 2-4 separately filtered and incubated overnight. The following day the filters are suspended in 50 ml of minimal media, diluted $10^{-2}$, $10^{-4}$, $10^{-6}$, and 0.1 ml aliquots are spread onto NO medium agar plates containing 5 mM m-toluate plus 100 μg/ml streptomycin. All transconjugants demonstrate a coinheritance of all TOL plasmid encoded functions. A single colony is purified and designated BACS 2-4 (pWWO).

2-Hydroxymuconic semialdehyde (HMSA) can be metabolized by either the Xyl F gene encoded enzyme (HMSA hydrolase) or by the Xyl G gene encoded enzyme (HMSA dehydrogenase). However, the corresponding metabolite in m-xylene metabolism, 2-hydroxy-6-keto-2,4-heptadienoic acid, can only be metabolized via the Xyl F gene encoded enzyme (HMSA hydrolase), whereas the Xyl G encoded enzyme is inactive towards this substrate.

On this basis, BACS 2-4 (pWWO) is mutagenized with NNG, selected against growth on m-toluate by amoxicillin and D-cycloserine enrichments, and plated onto 5 mM m-toluate plus 0.5 mM succinate. Small colonies are selected and tested for the inability to grow on m-toluate. At least one mutant accumulates the methyl ketone ring fission product from m-toluate. When this type mutant is grown on Luria broth plus toluene and assayed for enzymes of the TOL plasmid, it is found to be defective in Xyl F (HMSA hydrolase), but still retains a functional Xyl G gene encoded enzyme (HMSA dehydrogenase). In addition, this type of mutant strain is able to grow on toluene, benzoate, p-xylene, p-toluate, but does not grow on m-xylene or m-toluate. The strain with inactive Xyl F encoded enzyme (HMSA hydrolase) is designated WG49.

Strain WG49 is mutagenized with NNG, selected against growth on p-toluate by enrichment with amoxicillin and D-cycloserine, and plated on nutrient agar plus 5 mM p-toluate. A single yellow colony is observed out of 400,000 colonies examined. This colony is purified and found unable to grow on toluene, benzoate, p-xylene, p-toluate, m-xylene or m-toluate. However, an accumulation of a yellow metabolite is observed when the above substrates are supplemented in nutrient agar. When this mutant strain is grown on Luria broth plus toluene and assayed for enzymes of the TOL plasmid, it is found to be inactive in both the Xyl F encoded enzyme (HMSA hydrolase) and the Xyl G encoded enzyme (HMSA dehydrogenase), but retains an active Xyl E encoded enzyme (catechol 2,3-oxygenase). This strain is designated WG49.2 (CEL 2050) and had the genotype of cat B−(pWWO Xyl F−Xyl G−) Sm$^r$.

A WG49.2 (CEL 2050) type of mutant strain has been deposited with the American Type Culture Collection (12301 Parklawn Drive, Rockville, Md. 20852) in compliance with MPEP 608.01(p)C and has been accorded accession number ATCC 39213.

A reverted derivative of WG49.2 (CEL 2050) is obtained and designated WG49.2R (CEL 2051). This strain is mutagenized with NNG and subjected to amoxicillin D-cycloserine counter selection cycles, selecting against growth on p-toluate. The cycle is plated onto 5 mM p-toluate in nutrient agar and yellow colonies are selected, purified and tested for the appropriate phenotype. A mutant strain is obtained which is several orders of magnitude more genetically stable than the parent strain WG49.2 (CEL 2050).

The genetically stable strain is designated WG49.2R1 (CEL 2052), and has been deposited with the American Type Culture Collection (12301 Parklawn Drive, Rockville, Md. 20852) in compliance with MPEP 608.01(p)C and has been accorded accession number ATCC 39636.

Table I is a summary of strain designations and phenotype/genotype identification.

Table II is a list of NO media and Luria broth formulations.

TABLE I

| | STRAIN DESIGNATIONS | | |
|---|---|---|---|
| CEL Number | Strain | Phenotype*/Genotype | Parent |
| 2000 | MW 1200 | TOL+ BA+ | *Pseudomonas* |

TABLE I-continued

STRAIN DESIGNATIONS

| CEL Number | Strain | Phenotype*/Genotype | Parent |
|---|---|---|---|
| | | | *putida* Biotype A |
| 2019 | BAC | TOL$^-$ BA$^-$ | CEL 2000 |
| 2020 | BACS | TOL$^-$ BA$^+$ Sm$^r$ | CEL 2019 |
| 2024 | BACS 2-4 | TOL$^-$ BA$^-$ cat B Sm$^r$ | CEL 202 |
| 2034 | BACS 2-4 (pWWO) | TOL$^+$ BA$^+$ cat B Sm$^r$ | CEL 2020 X |
| | | | CEL 2115 |
| 2049 | WG49 | Xyl F cat B Sm$^r$ | CEL 2034 |
| 2050 | WG49.2 | Xyl F Xyl G cat B Sm$^r$ | CEL 2049 |
| 2051 | WG49.2R | Xyl F Xyl G$^r$ cat B Sm$^r$ | CEL 2050 |
| 2052 | WG49.2R1 | Xyl F Xyl G cat B Sm$^r$ | CEL 2051 |
| 2115 | PaW15 | TOL$^+$ leu | *Pseudomonas arvilla* mt-2 |

*TOL$^+$ Growth on toluene, m-xylene, p-xylene, benzoate, m-toluate and p-toluate.
BA$^+$ Growth on benzoate
Sm$^r$ Streptomycin resistant
Cat B Mutant in muconate lactonizing enzyme
Xyl F Mutant in HMSA hydrolase - tol$^+$ m-Xyl$^-$ p-Xyl$^+$
Xyl G Mutant in HMSA dehydrogenase - tol$^-$ m-Xyl$^-$ p-Xyl$^-$
Xyl G$^r$ Revertant in HMSA dehydrogenase - tol$^-$ m-Xyl$^-$ p-Xyl$^+$
leu leucine auxotroph

TABLE II

MEDIUM COMPOSITIONS

| Chemicals | (g/l) | (mM) |
|---|---|---|
| Regular "NO" Medium | | |
| Na$_2$HPO$_4$ | 7.1 | 50 |
| KH$_2$PO$_4$ | 13.6 | 100 |
| (NH$_4$)$_2$SO$_4$ | 2.25 | 17 |
| MgSO$_4$.7H$_2$O | 0.246 | 1 |
| CaCl$_2$ | 0.0111 | 0.1 |
| FeSO$_4$.7H$_2$O | 0.00278 | 0.01 |
| With growth carbon source in deionized water. | | |
| Modified "NO" Medium | | |
| Na$_2$HPO$_4$ | 7.1 | 50 |
| KH$_2$PO$_4$ | 13.6 | 100 |
| (NH$_4$)$_2$SO$_4$ | 0.281 | 2.1 |
| MgSO$_4$.7H$_2$O | 0.738 | 3 |
| CaCl$_2$ | 0.0222 | 0.2 |
| FeSO$_4$.7H$_2$O | 0.00834 | 0.03 |
| With growth carbon source in deionized water. | | |

| Luria Broth Ingredients | (g/l) |
|---|---|
| Bacto Tryptone (Difco) | 10 |
| Yeast extract (Difco) | 5 |
| Glucose | 1 |
| Sodium chloride | 8 |
| Calcium chloride | 0.22 |

EXAMPLE III

This Example illustrates the bioconversion of an aromatic substrate to an accumulated quantity of 2-hydroxymuconic semialdehyde with a microorganism of the type constructed in Example II.

A colony of strain CEL 2050 (ATCC 39213) from a nutrient agar plate is inoculated into 50 ml of NO medium containing 20 mM glucose and grown overnight. A 20 ml portion of this overnight culture is used to inoculate a 1750 ml fermentor containing a modified NO medium with 4.25 mM ammonium sulfate, 20 mM glucose and 0.1% antifoam. After growth to stationary phase due to nitrogen limitation (250-300 klett units), toluene is introduced by sparging liquid toluene with air at 0.3 cubic feet per hour.

Under both batch and continuous conditions, a transient accumulation of up to about 1.8 mM of 2-hydroxymuconic semialdehyde is observed, as determined by UV analysis (375 μm). The rate of 2-hydroxymuconic semialdehyde production observed is in the range between about 100-200 milligrams per liter of bioconversion medium per hour.

When a neutralized solution of sodium metabisulfite is added to a bioconversion system as described above, an accumulation of up to about 7.8 mM of 2-hydroxymuconic semialdehyde-bisulfite adduct is obtained.

Similar bioconversion to 2-hydroxymuconic semialdehyde is observed when the aromatic substrate is m-xylene, p-xylene, benzyl alcohol, benzoic acid or catechol in the bioconversion process.

EXAMPLE IV

This Example illustrates the bioconversion of toluene to an accumulated quantity of picolinic acid in accordance with the present invention process.

I.

A culture of strain CEL 2052 (ATCC 39636), growing continuously on 20 mM glucose and 8.5 mM nitrate, is induced with toluene in the absence of ammonium ions. 2-Hydroxymuconic semialdehyde is observed to accumulate rapidly at a rate which would produce 0.082 g/gdw/hr of picolinic acid if excess ammonium ions had been present. Instead, growth is inhibited immediately and the culture washes out at a dilution rate of 0.12 hr$^{-1}$.

This indicates that the accumulated quantity of 2-hydroxymuconic semialdehyde in the bioconversion medium has a growth inhibitory effect on strain CEL 2052.

II.

When excess ammonium ions are present in the fermentation broth in accordance with the present invention process, toluene is converted to 2-hydroxymuconic semialdehyde, which in turn reacts with the ammonium ions to produce an accumulating quantity of picolinic acid.

For optimum accumulation of picolinic acid, the strain CEL 2052 culture is grown continuously overnight on 120 mM acetic acid with 8.5 mM ammonium sulfate as the nitrogen source. The medium is buffered at pH 7.9 with 75 mM of phosphate salts. Toluene is introduced by sparging at 0.3 cfh, and after two hours the continuous addition of acetate is stopped and 50 mM ammonium sulfate is added. Acetate is added intermittently during the run, and is consumed without cell growth.

Up to 9 mM of picolinic acid is observed to accumulate at a specific rate of 0.067 g picolinic acid/gdw/hr (FIG. 1). This is in contrast to approximately 5 mM picolinic acid which accumulates when glucose plus nitrate are the carbon and nitrogen sources (FIG. 1).

Employing excess methylamine instead of excess ammonium ions yields the corresponding N-methyl quaternary picolinic acid product.

EXAMPLE V

This Example illustrates the bioconversion of catechol to an accumulated quantity of picolinic acid in accordance with the present invention process.

Strain CEL 2052 (ATCC 39636) is grown overnight in 1.0 liter of Luria broth in the presence of toluene. The culture is centrifuged and suspended in a medium containing 100 mM of ammonium sulfate and buffered at pH 8 with 150 mM of phosphate salts.

Figure 2:
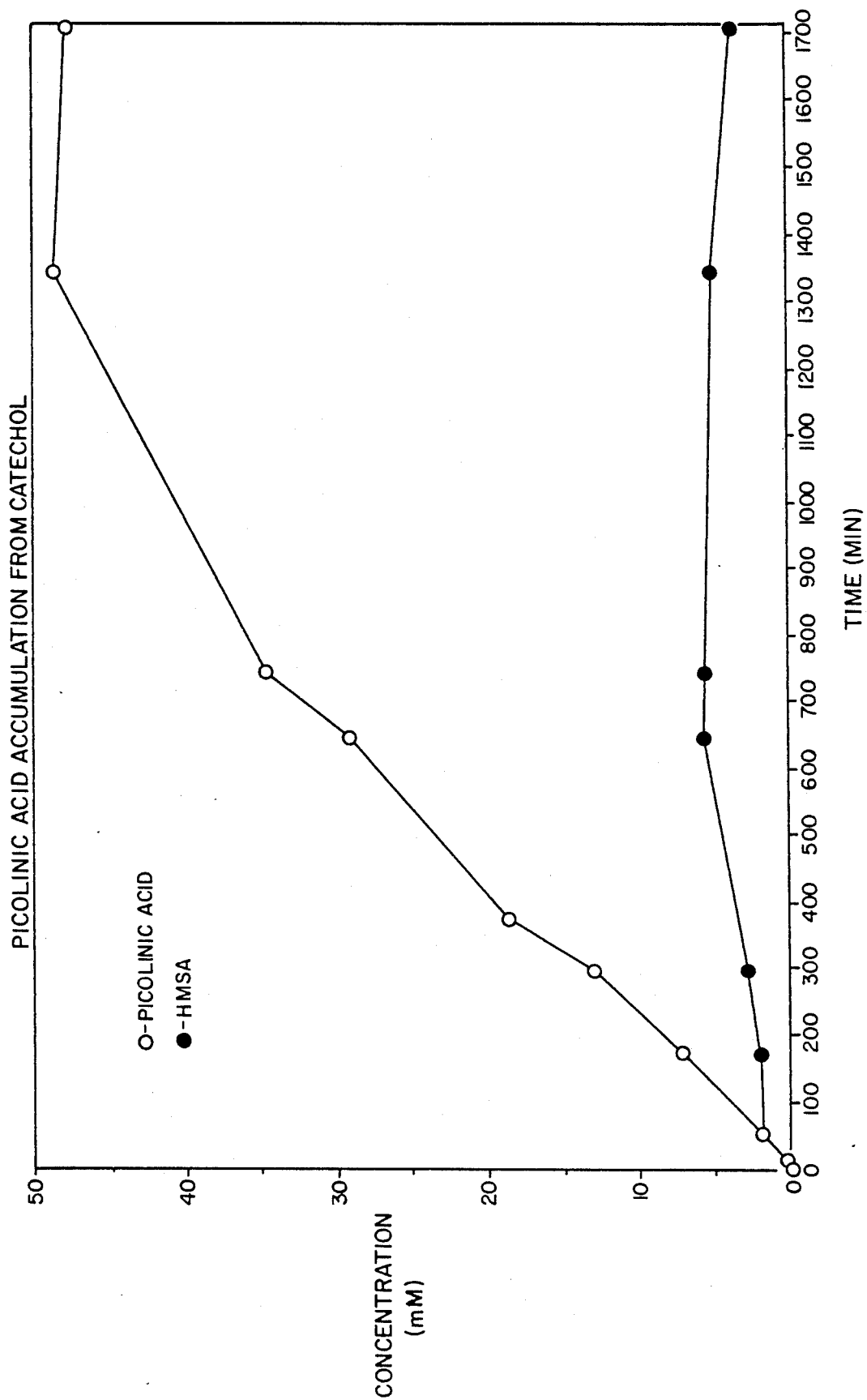

Catechol is added at 4.65 mM/hr, and oxygen tension is maintained at 5–10% of saturation. At this rate of catechol addition, the input of catechol is specific activity limiting. Picolinic acid accumulates up to 50 mM within 22 hours at a specific activity of 0.27–0.29 g/gdw/hr (FIG. 2). Since catechol addition is limiting, the observed specific activity represents a minimum value.

Similar bioconversion to accumulated picolinic acid is observed when the aromatic substrate is benzyl alcohol or benzoic acid.

EXAMPLE VI

This Example illustrates the chemical conversion of picolinic acid to pyridine.

A portion of bioconversion medium containing about one gram per liter of picolinic acid is per the Example IV procedure) is centrifuged to separate the whole cells from the aqueous phase. The separation is accomplished in a DuPont Sorvall RC53 model at 12,000 ×g for ten minutes employing a SS37 rotor.

The cell-free aqueous solution is acidified with hydrochloric acid to a pH of less than about 1.0. The acidified solution is transferred to an autoclave, and the solution is heated at 150° C. for five hours.

The aqueous solution is neutralized with sodium carbonate, and the pyridine product is recovered as a pyridine-water azeotrope by distillation.

What is claimed is:

1. In the process of preparing picolinic acid and alkyl substituted picolinic acid derivatives in which an alkyl substituted aromatic hydrocarbon and molecular oxygen are converted to a 2-hydroxymuconic semialdehyde in a bioconversion medium containing a Pseudomouas microorganism exhibiting catechol 2,3-oxygenase activity and the resultant 2-hydroxymuconic semialdehyde is thereafter reacted with ammonia or a primary amine, the improvement which comprises adding ammonium or a primary amine to the bioconversion medium during the bioconversion in an amount in excess of the microorganism's nutritional needs and at a rate sufficient to react in situ with said 2-hydroxymuconic semialdehyde and prevent accumulative levels of said 2-hydroxymuconic semialdehyde above about 1 g/Liter of bioconversion medium.

2. The process according to claim 1 wherein the microbial culture exhibits the taxonomic characteristics of ATCC 39636 strain of *Pseudomonas putida* Biotype A.

3. A process according to claim 1 wherein the aromatic hydrocarbon is toluene.

4. A process according to claim 1 wherein the aromatic hydrocarbon is m-xylene.

5. A process according to claim 1 wherein the aromatic hydrocarbon is p-xylene.

6. A process according to claim 1 wherein the bioconversion medium is buffered to provide an approximately neutral pH.

* * * * *